United States Patent
Cattani

[19]

[11] Patent Number: 6,083,306
[45] Date of Patent: Jul. 4, 2000

[54] SEPARATOR AND DISCHARGER DEVICE FOR WASTE FLUIDS IN DENTAL ASPIRATION APPARATUS

[75] Inventor: Ennio Cattani, Parma, Italy

[73] Assignee: Cattani S.p.A., Parma, Italy

[21] Appl. No.: 09/232,216

[22] Filed: Jan. 19, 1999

[51] Int. Cl.[7] .............................. B01D 19/00; A61C 17/06
[52] U.S. Cl. ............................. 96/157; 433/92; 604/319
[58] Field of Search ........................ 96/155, 157; 95/24; 604/319, 320; 433/92

[56] References Cited

U.S. PATENT DOCUMENTS

| | | |
|---|---|---|
| 3,964,112 | 6/1976 | Plowman . |
| 4,344,756 | 8/1982 | Folkenroth . |
| 4,684,345 | 8/1987 | Cattani . |
| 5,018,971 | 5/1991 | Trawoger et al. . |
| 5,797,742 | 8/1998 | Fraker . |

FOREIGN PATENT DOCUMENTS

| | | |
|---|---|---|
| 0480881 | 4/1992 | European Pat. Off. . |
| 0557251 | 8/1993 | European Pat. Off. . |

*Primary Examiner*—David A. Simmons
*Assistant Examiner*—Fred Prince
*Attorney, Agent, or Firm*—Browdy and Neimark

[57] ABSTRACT

The separator and discharger device for waste fluids in dental plants comprises a separator chamber internally of which a depression is created. A cannula aspirating fluids from a patient's mouth is connected to the separator chamber. Aspirated liquids are discharged into a bottom of the chamber and then removed by means of a drainage pump, while air sent into the separator chamber is extracted from an upper part of the chamber. The drainage pump, downstream of which a single-acting valve is located, is started up when a liquid level in the chamber reaches a predetermined level. The drainage pump is always started up in a state of full immersion in the liquid, even when the single-acting valve is malfunctioning.

4 Claims, 1 Drawing Sheet

SEPARATOR AND DISCHARGER DEVICE FOR WASTE FLUIDS IN DENTAL ASPIRATION APPARATUS

BACKGROUND OF THE INVENTION

Plants and apparatus of the type in object have the task of removing fluids from the patient's mouth during a dental operation. The fluids comprise a gassy part, usually air, and a liquid part, generally water and other liquids used in the dental apparatus, but there is also a solid part mostly containing particles of dental amalgam used in filling.

Many prior-art dental aspiration plants include a separator chamber in which a depression is created, for example by means of a suction pump. The tube aspirating the fluids from the patient's mouth is connected to the separator chamber, where the fluids are borne and deposited. These fluids are then discharged from the separator and sent to the sewers, while the air is extracted from the separator by the suction pump.

In some known methods, the liquids are extracted from the separator by a drainage pump which removes the liquids from the separator chamber—which is in depression—and discharges them into the environment at atmospheric pressure, for example into the municipal sewers.

A device of the above-described type is described and illustrated in European Patent EP 211808.

Downstream of the drainage pump there is usually a single-acting valve allowing only pump-to-environment liquid flow at atmospheric pressure, and closing the discharge pipe when the pump is not operating.

The single-acting valve, which is normally of the oscillating obturator type, can at times function faultily due to the fact that the liquids being extracted by the pump and discharged into the sewers contain solid particles (amalgam, encrustations, various residues) which can get lodged between the valve obturator and its seating and prevent the valve from closing properly when the pump is stopped. This can cause a back-flow of air into the discharge pipe due to the difference in pressure between the external atmosphere, kept at atmospheric pressure, and the separator chamber, which is in depression, with a possible consequent emptying of the liquid in the pump internal pipes. Lack of liquid can lead to considerable pump restart difficulties, and has led to pump design which allows for the possibility of restart even in the absence of liquids. These pumps, however, are expensive to build, run and maintain.

SUMMARY OF THE INVENTION

The main aim of the present invention is to obviate the above-mentioned drawback in the prior art, by providing a separator and discharger for waste fluids in dental aspiration equipment, wherein the drainage pump is kept immersed in liquid even when the single-acting valve downstream of the pump itself is malfunctioning.

An advantage of the device is that it is constructionally very simple and economical.

These aims and advantages and more besides are all achieved by the invention as it is characterised in the claims that follow.

BRIEF DESCRIPTION OF THE DRAWINGS

Further characteristics and advantages of the present invention will better emerge from the detailed description that follows of a preferred but non-exclusive embodiment of the invention, illustrated purely by way of a non-limiting example in the accompanying figures of the drawings, in which.

DESCRIPTION OF THE PREFERRED EMBODIMENTS

Figure 1:
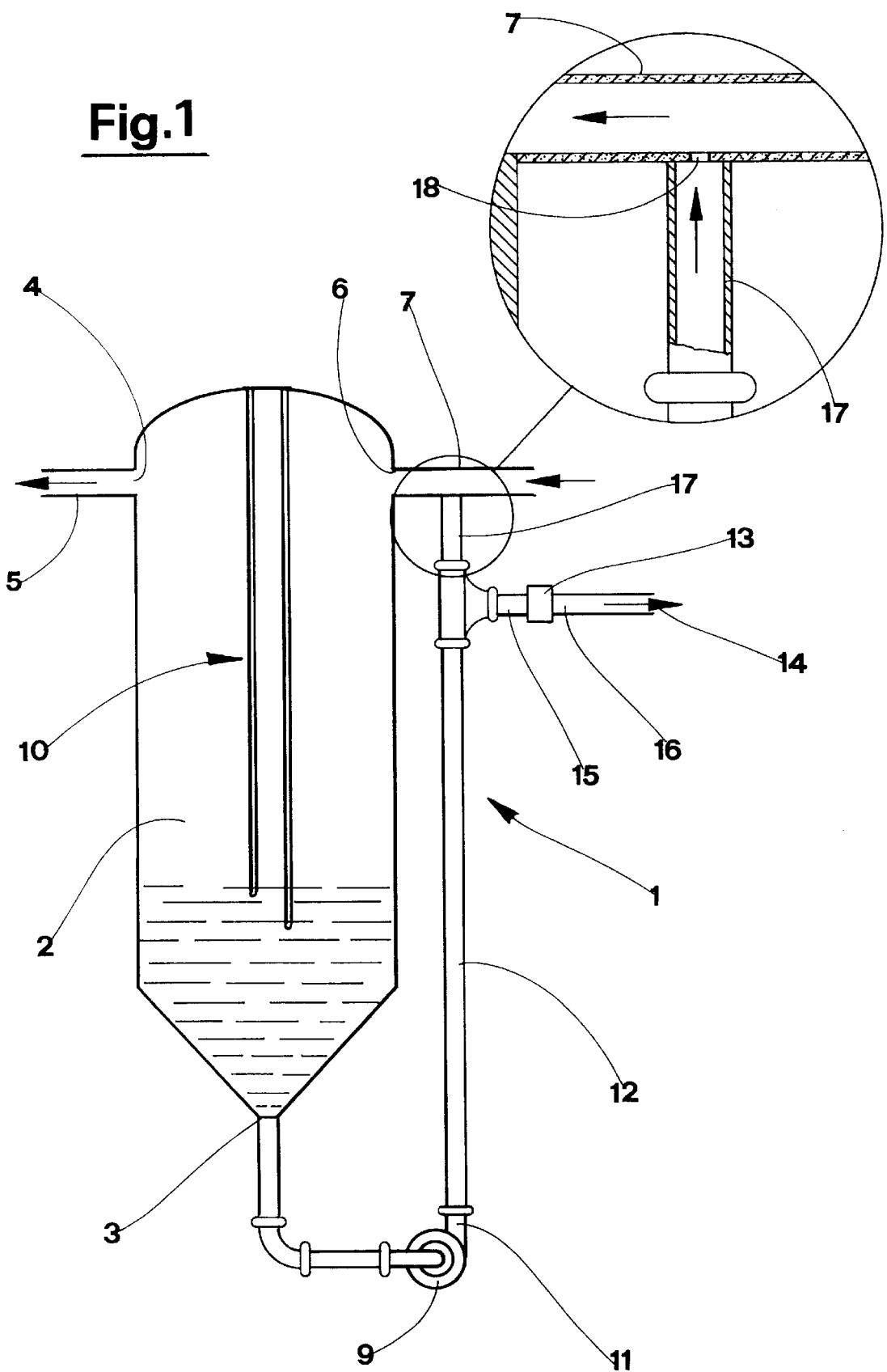
FIG. 1 is a schematic section in vertical elevation of a device made according to the present invention.

With reference to the FIG. 1 denotes in its entirety a separator and discharger device for waste fluids in dental aspiration apparatus.

The device 1 comprises a separator chamber 2 in which the dischargeable waste fluids coming from the patient's mouth are collected, and from which these waste fluids, apart from the gassy part thereof, are sent to the sewers. The separator chamber 2 is basically cylindrical in shape and exhibits a funnel-shaped bottom converging towards a discharge hole 3. The chamber 2 has at its top end a hole for gas discharge which is connected by a first suction pipe 5 to a suction pump of known type and not illustrated. The chamber 2 is further provided at its top end with a second hole 6 for fluid entrance through which the fluids produced by a dental apparatus (not illustrated) enter. The second hole 6 is conected by a second suction pipe 7 to a dental cannula or, should the apparatus used have more than one cannula, to the manifold of a dental instrument console, of known type, where the fluids produced by the various cannulas are collected.

The gassy part of the fluid entering the chamber 2 exits through the first hole 4, while the remaining part of the fluid collects therein.

A drainage pump 9 is predisposed beneath the separator chamber 2, which pump is activated on command and which enables liquids to be extracted from the separator device 1. The drainage pump 9 is normally still and enters into operation, commanded by suitable command means of known type, when the level of the liquid in the chamber 2 reaches a predetermined point. The command means generally comprise a probe system 10, of known type, which regulates the outlet and inlet of fluids into the chamber 2, i.e. the level of the liquids internally of the chamber 2. Two probes are shown in the illustrated example, whose connection wires can exit through the upper part (cover) of the chamber 2. By means of an electric command signal, the two probes operate the drainage pump 9 when they are both wetted by the liquid or by foam present inside the chamber 2, when that liquid or foam has reached the level the probes are set at. The probe pair also sends an electric command signal which stops the pump 9. This signal is sent when the level of the liquid inside the chamber 2 is not touching both probes; a timer is provided so that when the signal is received for stopping the drainage pump 9, a certain predetermined time lapse occurs before the pump 9 shuts down. A further, safety probe (of known type and not illustrated) could be provided in the probe system 10 for stopping pump operation when the liquid in the chamber 2 reaches the safety probe level.

In other words, the drainage pump 9 is started up and stopped by on and off signals depending on the level of the liquid in the separator chamber 2, and is kept in function by means of a timer for a predetermined period of time following receipt of the stop command, or off signal.

The drainage pump 9 exhibits an outlet 11 connected to a drainage pipe 12 in which a known-type single-acting valve 13 is placed, which valve 13 allows fluid movement only in one direction, indicated by arrow 14. With reference to the direction indicated by the arrow 14, the valve 13 exhibits an inlet 15 and an outlet 16. The single-acting valve 13 is located above the predetermined liquid level at which the probe system 10 starts up the drainage pump 9. The inlet 15 of the single-acting valve 13 communicates with the separator chamber 2 through a by-pass pipe 17 preferably provided with a choke opening 18, constituted for example by a calibrated hole of a few millimeters' diameter. In the described example the by-pass 17 opens into the second suction pipe 7 which in turn opens into the separator chamber 2. The by-pass can if so desired enter directly into the separator chamber 2. The by-pass 17 is located at a higher position than the tract of discharge pipe 12 which goes from the outlet 11 of the drainage pump 9 to the single-acting valve 13. The fluids removed from the separator chamber 2, by now without the gassy parts, are discharged directly into the sewers, or can be sent to a centrifuge, of known type and not illustrated, situated downstream of the single-acting valve 13, from the bottom of which the solid particles are removed and from the top of which the liquids, now filtered of solids, can be removed and sent to the sewers.

The device operation will now be described in detail.

When the suction pump is externally actuated, air is aspirated from inside the separator chamber 2, causing the pressure therein to drop progressively. The drop in pressure causes the single-acting valve 13 to close and the dentist's cannulas, being now connected up to a depressed atmosphere, can perform their proper task, i.e. aspirating liquids and other materials from the patient's mouth.

The aspirated fluid, consisting of air, liquids and solid particles, enters the separator chamber 2 through the inlet hole; the air, and in general the gassy parts, exit from the top of the separator chamber 2 through the gas exit hole 4, while the liquid part containing also the suspended solid particles falls to the bottom of the separator chamber 2 and is accumulated there.

The drainage pump 9 does not begin operating yet as the whole of the bottom part of the separator chamber can fill up before the probe system 10 is wetted and the pump 9 actuated.

When the liquid which continues to enter the separator chamber 2 reaches the probe system 10, the probes signal that the liquid in the chamber 2 has reached a certain predetermined level, and the pump 9 is accordingly actuated and begins to extract the liquids from the separator chamber 2. The operation of the pump 9 is stopped when the liquid in the separator chamber 2 reaches a predetermined minimum level.

During pump 9 operation a part of the liquid extracted from the pump can return to the separator chamber 2 through the by-pass 17 and the fluid inlet hole 6. The by-passed part of the liquid re-entering the chamber 2 is however small in comparison to the liquid which passes through the single-acting valve 13 and which is discharged there-from to the sewers (passing, if so designed, through the centrifuge or other known device). During this phase the choke 18 of the by-pass 17 has the task of reducing to a minimum the percentage of liquid which re-enters the chamber 2 after having been extracted there-from. The percentage of by-passed liquid re-entering is in any case too small to cause any hindrance to smooth device operation.

The adoption of a by-pass 17 for the liquid on the discharge pipe 12—preferably located immediately upstream of the single-acting valve 13—together with the fact of locating the single-acting valve 13 higher than the maximum level the liquid (or foam) can reach in the chamber 2, prevents the drainage pump 9 from emptying and having to re-start in a non-immersed state, even should the single-acting valve 13 be prevented from fully closing for any reason when the pump 9 is stopped.

Should the valve 13 not close completely, the discharge pipe 12 communicates with the inside of the chamber 2 (at lower pressure) through the by-pass 17, so that the pressure in the discharge pipe 12 becomes equal to that in the chamber 2, with the consequence that the level of liquid in the discharge pipe 12 is brought by the communicating-chambers principle to the same level as the liquid level in the chamber 2.

In this way the discharge pipe 12 never completely empties of liquid, and what is more, when the pump 9 re-starts the liquid level in the chamber 2 and in the discharge pipe 12 is the same, which guarantees that the pump 9 is always immersed.

When the single-acting pump 13 does not close perfectly when the pump 9 stops, for example due to the presence of solid particles, it can happen that during the time when the pump 9 is not working there is a suck-back of air through the by-pass 17 in a direction going from the tract of discharge pipe 12 situated downstream of the single-acting valve 13—which valve 13 is, as mentioned, at least partially open due to solid particles or other obstruction—towards the inside of the chamber 2. This is obviously due to the fact that the suction pump has to continue working to maintain the desired degree of depression inside the chamber 2. The suck-back of air from the discharge pipe 12 is however very small and does not constitute a problem for device 1 operation.

When the maximum level of liquid is once more reached inside the chamber 2, the drainage pump 9 (filly immersed in liquid) is restarted, which causes complete opening of the single-acting valve 13, thus freeing the obturator of the obstructing particle or particles.

What is claimed:

1. A separator and discharger device for waste fluids in dental aspiration apparatus, comprising:

a separator chamber internally of which a depression can be induced, connected to one or more cannulas for aspirating fluids from patients' mouths;

a drainage pump, connected to a bottom of the separator chamber, for extracting liquid from the separator chamber; said drainage pump having an outlet connected to a discharge pipe; a single-acting valve being located in said discharge pipe;

means for commanding the drainage pump, which means for commanding start the drainage pump whenever a level of liquid in the separator chamber (2) reaches a predetermined height;

wherein the single-acting valve is located above said predetermined height of the liquid level and exhibits an inlet which is in communication with the separator chamber through a by-pass pipe.

2. The device of claim 1, wherein the by-pass pipe has a narrowed passage section functioning as a choke.

3. The device of claim 1, wherein the by-pass pipe opens into a suction pipe which is connected to the cannula or cannulas aspirating fluids from a patient's mouth and which terminates in the separator chamber.

4. The device of claim 1, wherein the by-pass pipe is located at a height which is greater than a height of a tract of discharge pipe going from an outlet of the drainage pump to the single-acting valve.

* * * * *